United States Patent [19]

Cue, Jr.

[11] Patent Number: 4,632,993
[45] Date of Patent: Dec. 30, 1986

[54] PROCESS FOR MAKING 2-GUANIDINO-4-(2-METHYL-4-IMIDAZOLYL) THIAZOLE DIHYDROBROMIDE

[75] Inventor: Berkeley W. Cue, Jr., Gales Ferry, Conn.

[73] Assignee: Pfizer Inc., New York, N.Y.

[21] Appl. No.: 659,749

[22] Filed: Oct. 11, 1984

[51] Int. Cl.$^4$ .................. C07D 277/46; C07D 233/70
[52] U.S. Cl. .................................... 548/198; 548/190; 548/343
[58] Field of Search ............... 548/190, 336, 202, 146, 548/148, 198; 514/368, 370

[56] References Cited

U.S. PATENT DOCUMENTS 4,374,843 2/1983 La Mattina et al. ................ 514/370
4,435,396 3/1984 La Mattina et al. ................ 548/198

Primary Examiner—Donald G. Daus
Assistant Examiner—Stephen M. Kapner
Attorney, Agent, or Firm—Charles J. Knuth; Albert E. Frost; Robert K. Blackwood

[57] ABSTRACT

2-Guanidino-4-(2-methyl-4-imidazolyl)thiazole dihydrobromide and a one-pot, high yield process for its preparation from 2-methyl-4(or 5)-acetylimidazole.

6 Claims, No Drawings

PROCESS FOR MAKING 2-GUANIDINO-4-(2-METHYL-4-IMIDAZOLYL) THIAZOLE DIHYDROBROMIDE

BACKGROUND OF THE INVENTION

The present invention is directed to the dihydrobromide salt of 2-guanidino-4-(2-methyl-4-imidazolyl)-thiazole, and to a one-pot, high yield process for its preparation from 2-methyl-4(or 5)-acetylimidazole, a compound having essentially equivalent tautomeric forms:

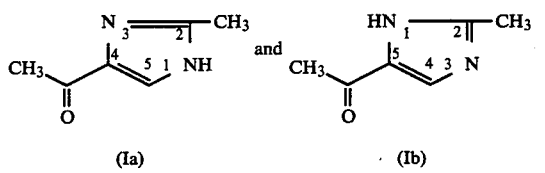

previously named 1-(2-methyl-4-imidazolyl)ethanone.

2-Guanidino-4-(2-methyl-4-imidazolyl)thiazole (or a pharmaceutically-acceptable salt thereof) is a highly potent histamine $H_2$ antagonist useful in the treatment of gastric hyperacidity and peptic ulcers (LaMattina and Lipinski, U.S. Pat. No. 4,374,843).

Heretofor, 2-guanidino-4-(2-methyl-4-imidazolyl)-thiazole has been generally disclosed in the form of pharmaceutically-acceptable salts (which would encompass the present dihydrobromide salt), but has been specifically described as its monohydrobromide salt (LaMattina and Lipinski, cited above), generally isolated in amorphous form. The form of 2-guanidino-4-(2-methyl-4-imidazolyl)thiazole presently employed clinically is the dihydrochloride salt, prepared from the present crystalline dihydrobromide salt via the free base. Heretofor, 2-guanidino-4-(2-methyl-4-imidazolyl)-thiazole was prepared (as said monohydrobromide salt) from 2-methyl-5-acetylimidazole in separate bromination and cyclization steps in an over-all yield of 40% (reflecting step yields of 51% and 79%).

SUMMARY OF THE INVENTION

Surprisingly, through the device of carrying out the bromination and cyclization steps in one pot (i.e. without isolation of the intermediate bromoacetyl compound) and having at least two equivalents of HBr present at the end of the cyclization step, we have been able to convert 2-methyl-4-acetylimidazole into 2-guanidino-4-(2-methyl-4-imidazolyl)thiazole dihydrobromide in about twice the previous over-all yield. Furthermore, the dihydrobromide is highly crystalline and of exceptional purity, eminently suitable for clinical use, or for conversion to base, dihydrochloride or another alternative salt form of like purity.

Thus, the present invention encompasses crystalline 2-guanidino-4-(2-methyl-4-imidazolyl)thiazole dihydrobromide per se, and a process therefor comprising (a) bromination of 2-methyl-4-acetylimidazole with substantially one molar equivalent of bromine in the presence of at least one molar equivalent of hydrobromic acid in a reaction inert solvent [preferably, either acetic acid or an excess of hydrobromic acid in concentrated aqueous form (e.g., 48% HBr)] preferably at 30°–90° C. (more preferably 40°–80° C.); (b) without isolation, cyclization of the intermediate 2-methyl-4-(bromoacetyl)imidazole in the resulting slurry or solution by reaction with substantially one equivalent of N-amidinothiourea in a reaction-inert solvent (preferably acetic acid or a combination of aqueous HBr and ethanol) preferably at 35°–100° C. (more preferably at 45°–90° C.); and (c) isolation of the resulting crystalline dihydrobromide salt by standard methods.

DETAILED DESCRIPTION OF THE INVENTION

According to the present invention 2-methyl-4-acetylimidazole of the formula

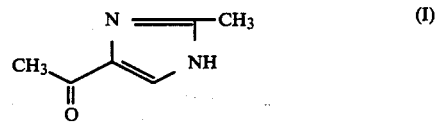

is readily converted, without isolation of intermediate 2-methyl-4-(bromoacetyl)imidazole of the formula

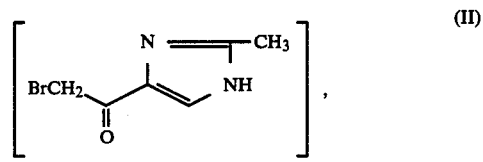

to a high yield of 2-guanidino-4-(2-methyl-4-imidazolyl)thiazole, of the formula

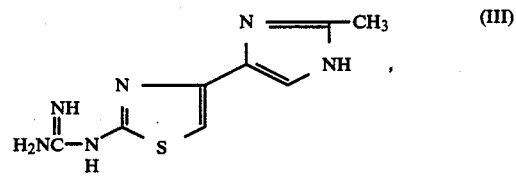

isolated in high over-all yield in the form of its crystalline dihydrobromide salt, of high purity and of excellent stability.

In the present one-pot bromination-cyclization process the bromination step is carried out by reaction of the compound (I) with substantially one equivalent of $Br_2$ in the presence of at least one equivalent of HBr (conveniently, concentrated aqueous HBr, such as 48% HBr) in a reaction-inert, preferably acidic solvent. Most preferred solvents are either acetic acid or an excess of concentrated aqueous HBr. Temperature is not critical, but is preferably in the range of 30°–90° C., high enough to obtain complete bromination within a reasonable time period and low enough to minimize formation of by-products. The most preferred temperature range is 40°–80° C.

As employed herein, the phrase "reaction-inert solvent" refers to a solvent which does not significantly interact with reactants, reagents, intermediates or product in a manner which significantly reduces the yield of the desired products.

The second step of the present one-pot process is carried out by combining the bromination reaction mixture, partially stripped of solvent if desired, with substantially one molar equivalent of N-amidinothiourea in the same or in combination with a second reaction-inert solvent such as a lower alkanol, preferably ethanol. Again, temperature is not critical, but for reasons delineated above for the bromination step, is preferably in the range 35°–100° C., most preferably in the range 45°–90° C., e.g. at the reflux temperature of the reaction mixture when aqueous HBr and ethanol are cosolvents for the cyclization step.

The crystalline 2-guanidino-4-(2-methyl-4-imidazolyl)thiazole dihydrobromide is separated from the reaction liquor by standard methods of filtration, centrifugation and/or decantation. If desired, the reaction mixture is partially stripped, chilled and/or digested prior to isolation.

The present invention is illustrated by the following examples. However, it should be understood that the invention is not limited to the specific details of these examples.

EXAMPLE 1

2-Guanidino-4-(2-methyl-4-imidazolyl)thiazole (Free Base)

2-Guanidino-4-(2-methyl-4-imidazolyl)thiazole monohydrobromide (360.7 g, 1.19 mole; U.S. Pat. No. 4,374,843) was slurried in 7500 ml $H_2O$ for 15 minutes at 19° C. With stirring, the pH was slowly adjusted from 5.8 to a stable value of 9.5 with 10% NaOH, 500±5 ml being required. After stirring a further 0.5 hours, title product was recovered by filtration on sintered glass. The sticky cake was washed with 2000 ml $H_2O$, pulled to a tight cake and finally washed with 1000 ml of hexane. After air drying on the funnel for 18 hours, the entire still-partially-wet cake was taken into the next step.

If required for formulation, the free base is dried to constant weight in vacuo, correcting for any remaining water in the formulation.

EXAMPLE 2

2-Guanidino-4-(2-methyl-4-imidazolyl)thiazole Dihydrochloride

The entire batch of partially-wet, free base of the preceding Example, presumed to contain the theoretical 265.3 g of free base on an anhydrous basis, was combined with 1030 ml of $CH_3OH$ and 4125 ml of isopropanol and heated to reflux. The hot solution was treated with 62 g activated carbon. After refluxing for 30 minutes, the hot mixture was filtered over diatomaceous earth with 2750 ml of hot isopropanol for wash. The combined filtrate and wash was diluted with an additional 2750 ml of isopropanol, now at 60° C. With stirring, concentrated HCl (345 ml) was added in a thin stream. The resulting suspension was concentrated to 2750 ml in vacuo, chased with 5500 ml of isopropanol while maintaining that volume, cooled to 0°–5° C., stirred 1.5 hours at that temperature, and title product recovered by filtration, washed with 700 ml cold isopropanol and dried in vacuo at ambient temperature; 307.2 g (87%) over two steps, m/e 222; u.v. lambda max. (0.01N $HCl/CH_3OH$) 229 and 260 nm ($E_1\,_{cm}$1% 661 and 569); lambda max. (0.01N $NaOH/CH_3OH$) 248 and 274 nm ($E_1\,_{cm}$1% 681 and 475); neutralization equivalent (1:1 ethanol: $H_2O$ with 0.5N NaOH) calcd. 295.2; found 299.9.

Analysis calculated for $C_8H_{10}N_6S.2HCl$: C, 32.55; H, 4.10; N, 28.47; S, 10.86; Cl−, 24.02%. Found: C, 32.30; H, 4.06; N, 28.29; S, 11.05; Cl−, 24.05%.

Alternatively, free base (10.0 g, 0.045 mol, weight corrected for up to 20% water content) was dissolved in 100 ml of hot glacial acetic acid, an amount just sufficient for complete dissolution at near reflux temperature. The hot solution was diluted with 10 ml additional hot acetic acid and then 7.5 ml (0.090 mol) of concentrated HCl was added. Title product, which began to crystallize almost immediately, was recovered by filtration after cooling to room temperature, and dried in vacuo at 40° C.; yield 12.63 g (95%), identical with the product crystallized from isopropanol.

Alternatively, free base (1.0 g, 0.0045 mol) was dissolved in 2 ml concentrated HCl. The dihydrochloride crystallized almost immediately. The mixture was diluted with 5 ml acetone, stirred 5 minutes, and title product recovered by filtration with acetone wash, 1.15 g (86.6%), identical with the product of Method A above.

Analysis calculated for $C_8H_{10}N_6S.2HCl$: C, 32.55; H, 4.10; N, 28.47%. Found: C, 32.16; H, 4.40; N, 28.09%.

EXAMPLE 3

2-Guanidino-4-(2-methyl-4-imidazolyl)thiazole Dihydrobromide

Method A

2-Methyl-4-acetylimidazole (4.00 g, 0.0322 mol; U.S. Pat. No. 4,374,843) was dissolved in 48% HBr (40 ml, 0.351 mol), the temperature rising to 33° C. The solution was heated to 50° C. $Br_2$ (1.65 ml, 5.15 g, 0.0322 mol) in 5 ml of 48% HBr was added dropwise over 17 minutes maintaining that temperature with external heating as necessary. The stirred reaction mixture was heated to 65° C. for 1.5 hours, cooled and stripped to a cream-colored slurry. The mixture was chased 2×20 ml $H_2O$ (the solids dissolving and returning to a thick slurry each time). Without further isolation of the intermediate 2-methyl-4-(bromoacetyl)imidazole, absolute ethanol (29.2 ml) was added, and then N-amidinothiourea (3.81 g, 0.0322 mol) and the slurry heated to reflux. The resulting solution was refluxed for 2 hours, by which time there was heavy precipitation of crystalline title product. The slurry was distilled to half-volume, cooled to room temperature, and title product recovered by filtration with a small amount of ethanol wash and dried at 35° C. in vacuo; 10.12 g (79% over two chemical steps); homogeneous by tlc Rf 0.75 (19:1 ethanol:concentrated $NH_4OH$); m.p. 300° C. (decomposition).

Analysis calculated for $C_8H_{10}N_6S.2HBr.0.5H_2O$: C, 24.44; H, 3.33; N, 21.38%. Found: C, 24.20; H, 3.18; N, 21.43%.

Method B

In the manner of Method A, 2-methyl-4-acetylimidazole (4.00 g, 0.0322 mol) was brominated, but with substitution of 3.67 ml (0.0322 mol) of 48% HBr and 4 ml of acetic acid for the initial charge of 48% HBr, and charging the $Br_2$ (1.65 ml) in 4 ml of acetic acid in place of 48% HBr. At the end of the 1.5 hour heating period (without cooling, stripping and chasing), the N-amidinothiourea (3.81 g) was added. The reaction exothermed from 67° to 77° C., and the resulting solution was heated at 80° C. for 1 hour during which title product began to precipitate heavily. Title product was recovered as in Method A, 9.34 g (73% over two chemical steps), identical with the product of Method A.

Method C

To 48% HBr (16.9 ml) was added 2-methyl-4-acetylimidazole (7.36 g, 0.059 mol) to form a clear yellow solution. $Br_2$ (3.0 ml, 0.059 mol) in 48% HBr (3.3 ml) was added dropwise as the reaction was warmed to 45° C. Transient precipitation was noted during addition and heating. After stirring for 18 hours at 45° C., the reaction mixture was cooled to 30° C., diluted with 22 ml absolute ethanol, and N-amidinothiourea (7.0 g) was added. The resulting slurry almost became clear, then set up to solids which were broken up with a spatula. The resulting mobile slurry was stirred at 55° C. for 2 hours, cooled to 10° C., and title product recovered by filtration with 2×5 ml absolute ethanol wash, 20.3 g (86%), identical with title product of Method A.

EXAMPLE 4

2-Guanidino-4-(2-methyl-4-imidazolyl)thiazole (Free Base)

2-Guanidino-4-(2-methyl-4-imidazolyl)thiazole dihydrobromide (13.4 g) was stirred with 66.9 ml $H_2O$ and the pH slowly adjusted to a stable value of 10.0 over 2 hours with 22.6 ml of 3N NaOH while maintaining a temperature of 22°-24° C. Title product was recovered by suction filtration with water wash, pulled to a tight cake under a rubber dam, repulped in 28 ml acetone for 2 hours, refiltered, washed with 12 ml acetone and dried at 40° C. in vacuum to yield crystalline title product, 8.66 g, containing about 15% water.

Anhydrous free base was prepared from water-wet cake (prepared as above, without acetone repulp) by dissolving 4.04 g of the water-wet cake (estimated to contain 1.60 g of free base on a dry basis) in 80 ml of refluxing acetone, treating the solution with 0.16 g activated carbon, filtering hot, concentrating the filtrate to 15 ml, stirring at room temperature for 1 hour, filtering with acetone wash and drying the cake at 40° C. in vacuo; yield: 1.57 g.

I claim:

1. A process for the preparation of 2-guanidino-4-(2-methyl-4-imidazolyl)thiazole dihydrobromide which comprises the steps of:
    (a) bromination of 2-methyl-4-acetylimidazole with substantially one molar equivalent of $Br_2$ in the presence of at least one molar equivalent of HBr in a reaction-inert solvent at 30° to 90° C.;
    (b) reaction of the resulting acidic slurry or solution of 2-methyl-4-(bromoacetyl)imidazole with substantially one molar equivalent of N-amidinothiourea at 35°-100° C. in the same or another reaction-inert solvent; and
    (c) isolation of said dihydrobromide salt from the resulting reaction mixture.

2. A process of claim 1 wherein only substantially one molar equivalent of HBr is employed in step (a), and the reaction-inert solvent in both steps (a) and (b) is acetic acid.

3. A process of claim 1 wherein the reaction-inert solvent of both steps (a) and (b) comprises concentrated aqueous HBr and the reaction-inert solvent in step (b) further comprises ethanol.

4. A process of claim 1 wherein step (a) is carried out at 40°-80° C.

5. A process of claim 1 wherein step (b) is carried out at 45°-90° C.

6. A process of claim 4 wherein step (b) is carried out at 45°-90° C.

* * * * *